(12) United States Patent
Kukuk et al.

(10) Patent No.: US 9,370,627 B2
(45) Date of Patent: Jun. 21, 2016

(54) NEEDLE GUIDANCE WITH A DUAL-HEADED LASER

(75) Inventors: Markus Kukuk, Palo Alto, CA (US); Adam K. Galant, Carpentersville, IL (US); Sandy Napel, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1155 days.

(21) Appl. No.: 11/829,345

(22) Filed: Jul. 27, 2007

(65) Prior Publication Data

US 2008/0200876 A1 Aug. 21, 2008

Related U.S. Application Data

(60) Provisional application No. 60/890,700, filed on Feb. 20, 2007.

(51) Int. Cl.
*A61B 5/05* (2006.01)
*A61M 5/42* (2006.01)
*A61B 18/20* (2006.01)

(52) U.S. Cl.
CPC ........ *A61M 5/427* (2013.01); *A61B 2018/2025* (2013.01)

(58) Field of Classification Search
CPC .......................... A61B 5/05; A61B 2018/2025
USPC ............................ 600/425, 427, 429; 606/130
See application file for complete search history.

(56) References Cited

U.S. PATENT DOCUMENTS

| | | | |
|---|---|---|---|
| 5,957,933 A * | 9/1999 | Yanof et al. | 606/130 |
| 6,049,582 A | 4/2000 | Novab | |
| 6,260,999 B1 | 7/2001 | Wofford et al. | |
| 6,605,095 B2 * | 8/2003 | Grossman | 606/130 |
| 6,811,313 B2 | 11/2004 | Graumann et al. | |
| 7,065,393 B2 | 6/2006 | Sati et al. | |
| 2006/0039537 A1 | 2/2006 | Strobel | |

OTHER PUBLICATIONS

Anderson, J., et al., "Virtual Reality Training in Interventional Radiology", Seminars in Interventional Radiology, 19(2), 2002.
Racadio, J., "Live 3D Guidance with XperGuide", Koninkijke Philips N.V., 2006.

* cited by examiner

*Primary Examiner* — Peter Luong

(57) ABSTRACT

Disclosed are method and apparatus for guiding a needle during an interventional radiology procedure. The target and skin entry point are pre-determined in three-dimensional medical imaging scans. The needle trajectory is defined by the target and skin entry point, which is physically marked on the skin. A dual-headed laser emitting two laser beams is positioned and aligned such that one laser beam is aimed at the skin entry point and the other laser beam is aimed at an external reference point, which is determined such that the axis of the laser beam aimed at the skin entry point is substantially collinear with the needle trajectory. The needle is inserted while maintaining the axis of the needle substantially collinear with the axis of the laser beam aimed at the skin entry point.

21 Claims, 9 Drawing Sheets

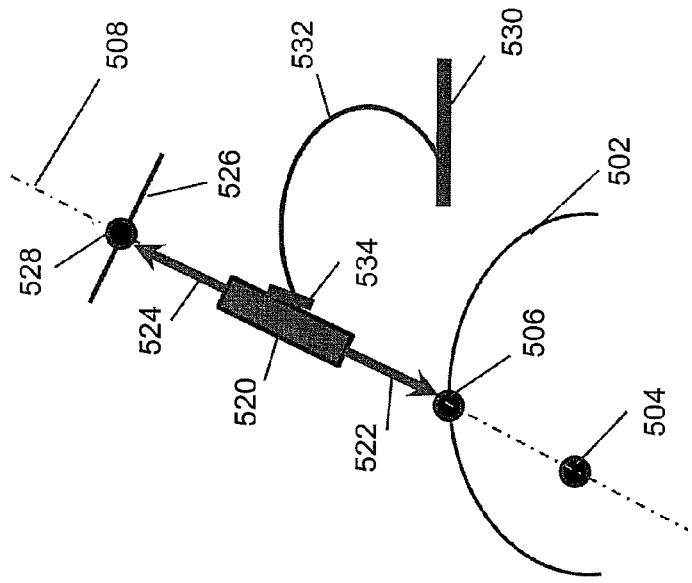
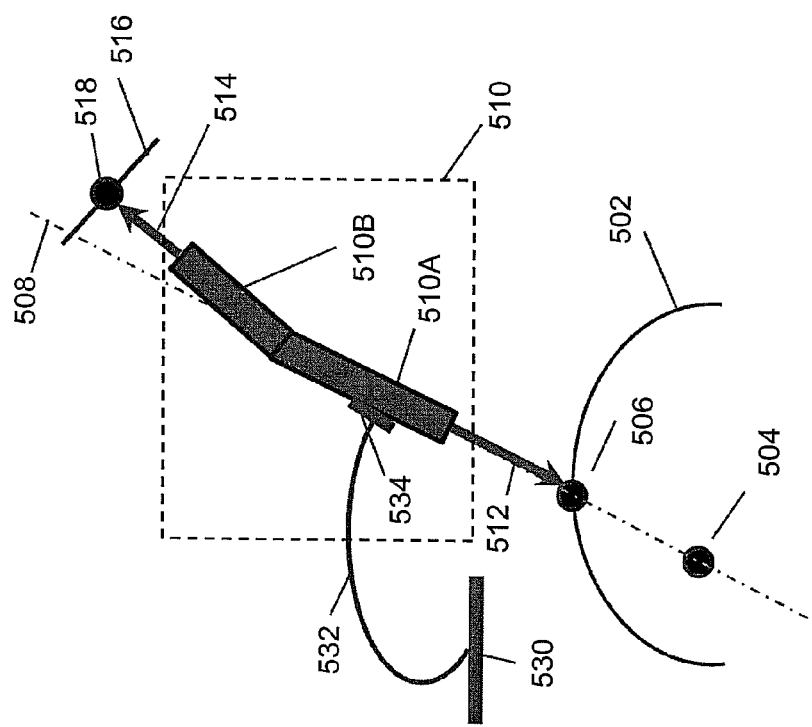
Fig. 5B
Fig. 5A

NEEDLE GUIDANCE WITH A DUAL-HEADED LASER

This application claims the benefit of U.S. Provisional Patent Application Ser. No. 60/890,700, filed on Feb. 20, 2007, which is incorporated herein by reference.

BACKGROUND

The present invention relates generally to interventional radiology, and more particularly to needle guidance.

Interventional radiology (IR) permits minimally invasive diagnostic and surgical procedures. In an IR procedure, medical imaging techniques allow a radiologist (or other medical staff) to guide small surgical instruments or devices into the region of interest in a patient. Examples of medical imaging techniques include X-Ray fluoroscopy, X-Ray computed tomography (CT), and magnetic resonance imaging (MRI). Examples of regions of interest include blood vessels and organs such as a heart or liver. One category of procedures is referred to as percutaneous (through the skin). In a typical percutaneous procedure, a hollow needle punctures the skin, the needle is inserted, and the tip is positioned in the region of interest. Through the hollow needle, various chemicals may be injected, and various surgical devices may be inserted. For example, in chemotherapy, therapeutic agents are injected into a tumor. In biopsy, a small sample of tissue is removed for laboratory examination.

The success of percutaneous procedures depends strongly on proper insertion of the needle into the region of interest. During insertion, the needle must be properly guided to minimize damage to surrounding tissue and blood vessels. Proper treatment requires precise placement of the tip of the needle. Insertion and placement are controlled primarily by two geometrical factors: the location of the region of interest and the skin entry point for insertion of the needle. The orientation of the needle is defined by the positions of the region of interest and the skin entry point.

In a common procedure, the patient is initially diagnosed with a three-dimensional imaging technique such as C-arm CT or MRI scan. The measurements are digitized and stored as data, often referred to as a "three-dimensional (3-D) volume dataset". From the 3-D volume dataset, an image processing system may be used later to render various 3-D and two-dimensional (2-D) views to locate a point in the region of interest (for example, a tumor) and a suitable skin entry point. The desired needle trajectory is defined by these two points. During the interventional procedure, the patient is imaged via live X-Ray fluoroscopy, which produces a 2-D projection image on a detector screen. The live 2-D X-Ray fluoroscopy image and the images rendered from the 3-D volume dataset acquired earlier are superimposed on a display to display the proper trajectory along which the needle is to be inserted. A precise method is then required to guide the needle along the intended trajectory. Some prior-art methods may not provide proper precision. Other prior-art methods may require a complicated sequence of steps. Two examples of prior-art methods are described below. Complicated procedures should be avoided because they extend the time during which the patient is subjected to the interventional surgical procedure. What is needed is a simple, quick, and precise method for guiding a needle during insertion in interventional percutaneous procedures.

SUMMARY

The location of a target in the region of interest and a skin entry point are pre-determined (for example, by a radiologist examining 3-D images). The desired needle trajectory is the line defined by the target location and the skin entry point. During an IR procedure, 3-D images of the target and skin entry point are rendered from a previously stored 3-D volume dataset and displayed on a monitor. The skin entry point is physically marked on the patient. A dual-headed optical source emitting two collimated beams is positioned and aligned such that one collimated beam is aimed at the skin entry point, and the other collimated beam is aimed at an external reference point. The external reference point is calculated such that the axis of the collimated beam aimed at the skin entry point is substantially collinear with the desired needle trajectory. The dual-headed optical source is mounted on a mechanical arm. The mechanical arm is loosened to position and align the collimated beams, and then the mechanical arm is locked in place. The needle is inserted such that the axis of the needle is maintained to be substantially collinear with the axis of the collimated beam aimed at the skin entry point.

In an advantageous embodiment, the two collimated beams are laser beams, with substantially collinear axes, pointing in opposite directions. The physical skin entry point is located by a combination of live X-Ray fluoroscopy and 3-D images rendered from previous measurements. The external reference point is calculated with a C-arm X-Ray system, which positions an X-Ray detector such that a visual index mark on the X-Ray detector is positioned at the calculated external reference point.

These and other advantages of the invention will be apparent to those of ordinary skill in the art by reference to the following detailed description and the accompanying drawings.

BRIEF DESCRIPTION OF THE DRAWINGS

FIG. 5A shows a schematic of a needle guidance system with a generic dual-headed optical source;
FIG. 5B shows a schematic of a needle guidance system with a collinear dual-headed laser.

DETAILED DESCRIPTION

Embodiments of the invention are described herein using a C-arm X-Ray system for illustration. One skilled in the art may develop embodiments applicable to other medical imaging systems.

Figure 1:
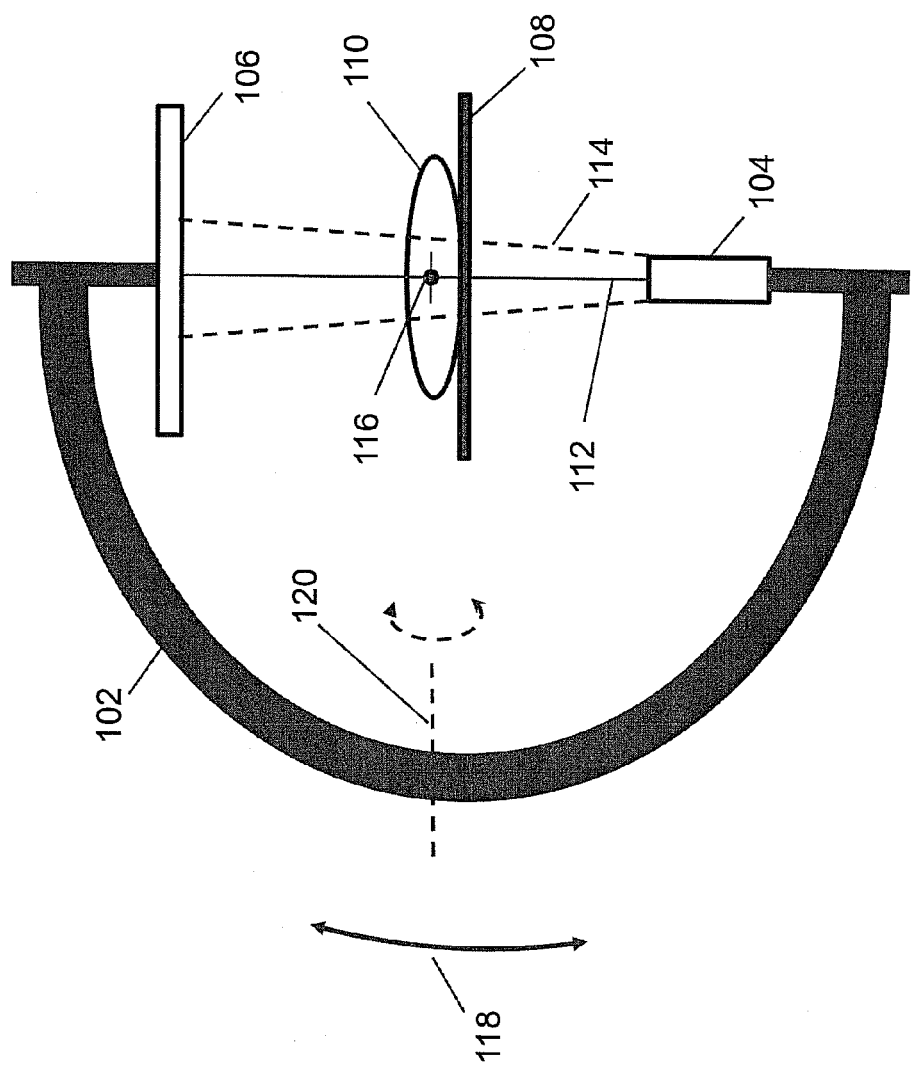
FIG. 1 shows a schematic of a C-arm X-Ray system.

As shown in the schematic in FIG. 1, a C-arm X-Ray system comprises a C-arm 102, an X-Ray source 104 mounted at one end of the C-arm 102, and an X-Ray flat-panel detector 106 mounted at the other end. More details of the detector are described below. A patient 110 is positioned on a table 108 such that X-rays emitted by the source 104 pass through the patient 110 and impinge on the detector 106 to create a 2-D image of the region of interest in the patient 110.

The image is digitized, and the data is stored in an image processing system. Herein, a "C-arm X-Ray system" further comprises any electronics, computer, software, image processing system, display, and user interface needed to control operation of the C-arm X-Ray system and to process the collected data. For simplicity, these elements are not shown in FIG. 1.

The C-arm 102 may be rotated about multiple axes to create multiple cross-sections of the patient 110. For example, the C-arm 102 may be rotated about an axis orthogonal to the plane shown in FIG. 1. This rotation is indicated by the double arrows 118. The C-arm 102 may also be rotated about axis 120, which lies in the plane of the C-arm 102. From the aggregate data of multiple scans, the image processing system may reconstruct the 3-D volume dataset and render various images representing 3-D views of the acquired dataset. These views include perspective views and various 2-D cross-sectional images of the patient's body. The images are typically viewed on a computer display. Herein, the 3-D volume dataset represents a 3-D numerical array whose elements hold the values of specific physical properties at points in space inside the patient's body. By assigning values of optical properties (such as, color and luminance) to the values of the physical properties, computer images are rendered to visualize the values of the physical properties inside the patient's body. Herein, these computer images are referred to as "3-D images".

The intersection of the rotation axes of the C-arm 102 is referred to as the isocenter. In practice, the isocenter is a small region, and not a single point. If the C-arm system is properly aligned, the isocenter is stationary as the C-arm 102 is rotated. The X-Ray beam emitted by X-Ray source 104 is shaped like a cone, in which all the rays originate from a focal point inside the source (for example, an X-Ray tube). Dashed line 114 represents an oblique X-Ray ray. Line 112 represents the axial X-Ray ray. Herein, to simplify the terminology, an "oblique X-Ray ray" will be referred to simply as an "oblique ray", and the "axial X-Ray ray" will be referred to simply as the "axial ray". The axial ray 112 passes through the isocenter 116 and impinges orthogonally on the plane of the detector 106.

Figure 2:
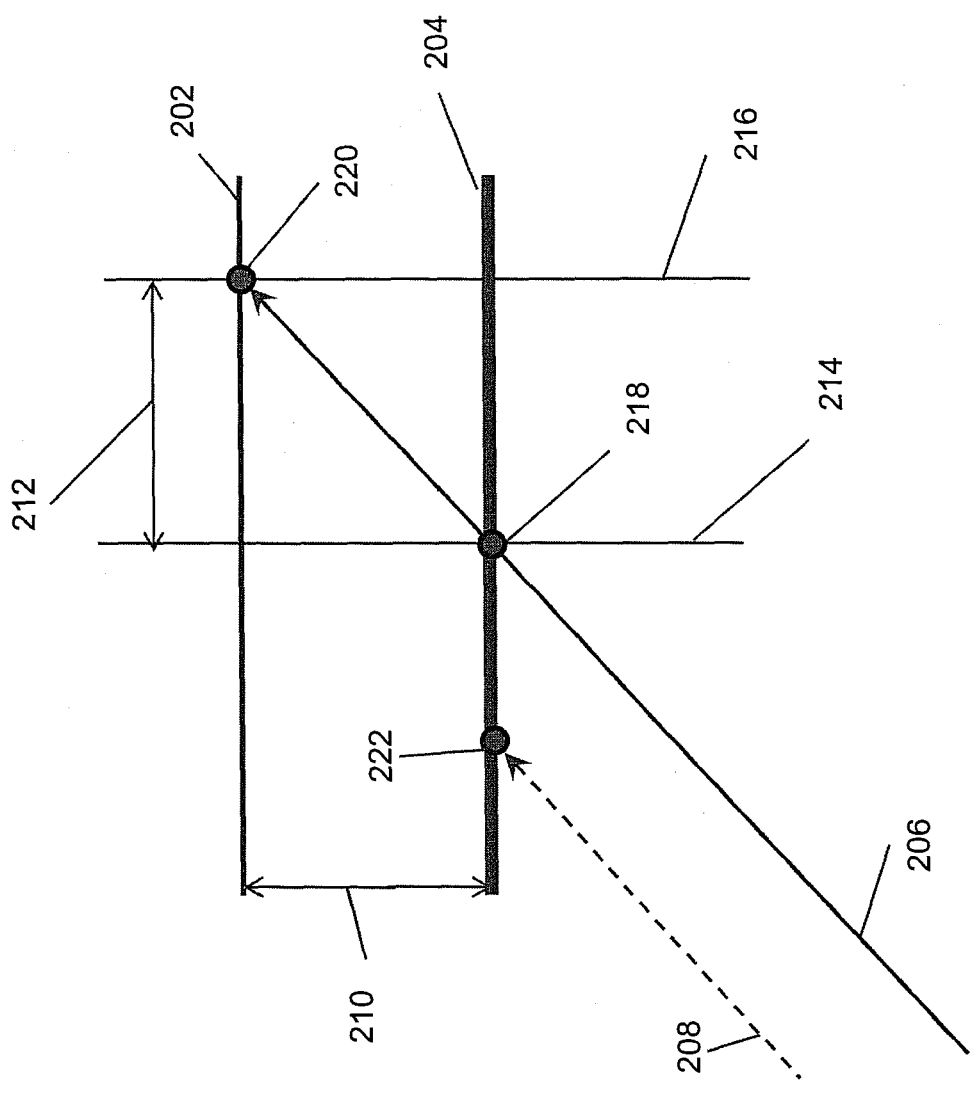
FIG. 2 shows a schematic of an X-Ray detector geometry.

FIG. 2 shows a cross-sectional view orthogonal to the plane of the flat-panel detector 106. Detector 106 comprises two major components: an X-Ray sensor array 202 and a protective cover 204. The cover 204 is optically opaque, but radiolucent (transparent to X-Rays). Sensor array 202 and cover 204 are separated by the orthogonal distance 210. In procedures described below, both X-Rays and light impinge on detector 106. The geometry of the detector needs to be taken into account during needle guidance procedures. Line 214 and line 216 are reference lines orthogonal to the plane of detector 106. An optical beam, such as a laser beam 208, impinges on detector 106 at a point 222 on the cover 204. Visual index marks, such as those used for optical alignment, are located on cover 204.

Axial ray 206, however, passes through cover 204 and impinges on detector 106 at point 220 on the sensor array 202. Point 218 and point 220 are separated by the (in-plane) lateral distance 212. X-Ray alignment is referenced with respect to point 220. In procedures described below, the center pixel of sensor array 202 is used as reference point 220. Other positions on sensor array 202, however, may be used for reference point 220. Since X-Ray alignment controls the needle guidance procedure, the offset between a point 218, which is visually marked on cover 204, and point 220, the corresponding point on sensor array 202, needs to be accounted for. One skilled in the art may use mathematical or mechanical procedures to correct for the offset. To simplify the examples described below, however, the sensor array 202 and cover 204 are assumed to be co-planar. That is, the orthogonal distance 210 and the lateral distance 212 are both assumed to be zero, and point 218 and point 220 are assumed to be coincident.

Prior-art procedures have used a laser for needle guidance. A laser impinges on the skin entry point such that the axis of the laser beam is collinear with the desired needle trajectory. The tip of the needle is first positioned on the skin entry point. The needle is then aligned with the laser beam. Details of alignment are described below. As the needle is inserted into the patient, alignment of the needle with the laser beam is maintained to guide the needle along the proper trajectory. More details of the procedure are provided below.

Figure 3:
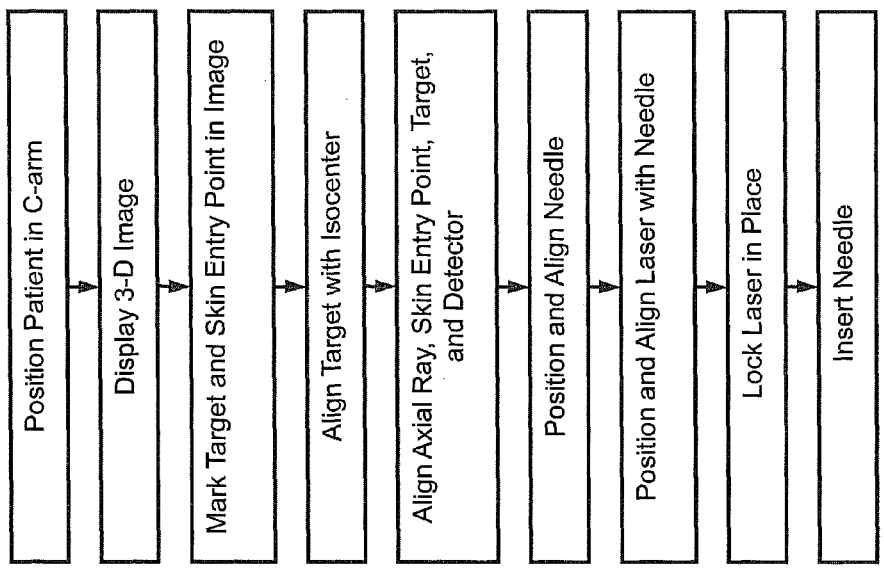
FIG. 3 shows a flowchart of a prior-art "bulls-eye view" procedure.

FIG. 3 shows a flowchart for a prior-art procedure, referred to as a "bulls-eye view" or "down-the-beam view" method. This method uses a C-arm X-Ray system. In step 302, a patient 110 is placed on table 108 and positioned in C-arm 102. In step 304, a 3-D image of the patient is rendered from a previously acquired 3-D volume dataset and displayed on a monitor. Diagnostics from previous examinations have already determined the target, skin entry point, and desired needle trajectory. Herein, "skin entry point" refers to the position on a patient's skin at which a needle is inserted. Herein, "target" refers to a point in the region of interest in the patient. The target is positioned "below the skin" within the body of the patient. As discussed previously, examples of a region of interest include a heart, a liver, and a blood vessel. Herein, an "external" point is positioned "above the skin" outside the body of the patient. Herein, "needle trajectory" refers to desired needle trajectory defined by the line running through the skin entry point and the target. Herein, "needle guidance" refers to a method for guiding a needle along the needle trajectory as the needle is inserted between the skin entry point and the target. Herein, in general, "needle" refers to an object which may pierce the skin, tissue, and other body parts of a patient. For example, "needle" may refer to a drill bit. In general, a needle may have a solid or a hollow body of arbitrary shape. In the examples below, a needle has an elongated, tapered body with a longitudinal axis along the elongated side of the needle. Herein, the longitudinal axis of the needle is referred to simply as the "axis" of the needle. In general, a needle has a pointed tip which pierces the skin. Herein, the end of the needle opposite the pointed tip is referred to as the "upper end" of the needle.

In step 306, the positions of the target and skin entry point are marked in the 3-D image with graphical markers. In step 308, the table 108 is moved to align the target with the isocenter 116. In step 310, C-arm 102 is rotated until the axial ray 112 from X-Ray source 104 is aligned with the skin entry point, target, and the center pixel of detector 106. This geometry generates a "bulls-eye" view on the display monitor. That is, the target and skin entry point are superimposed on top of each other, and the axial ray 112 and the planned needle trajectory are collinear.

In step 312, the patient 110 is viewed under live fluoroscopy, and the live fluoroscopic image is superimposed onto the 3-D image and displayed on the monitor. The tip of a needle is placed on the skin of the patient 110 and moved until the tip, as viewed on the fluoroscopic image, coincides with the skin entry point, as viewed on the 3-D image. The skin entry point is marked on the patient 110 with a physical marker, such as a pen. The needle is not inserted at this time. Under live fluoroscopy, the orientation of the needle is adjusted until the axis of the needle is collinear with the axial ray. When the axis of the needle is not collinear, the projection of the needle on the display is a line. When the axis of the needle is collinear, the projection of the needle on the display is a point. In step 314, a single-headed laser, which may be mounted on a mechanical arm, is positioned above the needle, such that the laser beam impinges on the skin entry point. The orientation of the laser is adjusted until the axis of the laser beam is collinear with the axis of the needle. In step 316, the laser is locked into place. Finally, in step 318, the needle is inserted while maintaining the axis of the needle collinear with the axis of the laser beam.

The above prior-art procedure has several disadvantages. Accurate alignment of the target with the isocenter is a difficult and lengthy procedure. The range of trajectories which may be configured by this procedure may also be restricted by the limited range of motion of table 108. Positioning and alignment of the laser by first positioning and aligning a needle under live fluoroscopy is also a difficult and time consuming procedure, which may require two people to perform.

Figure 4:
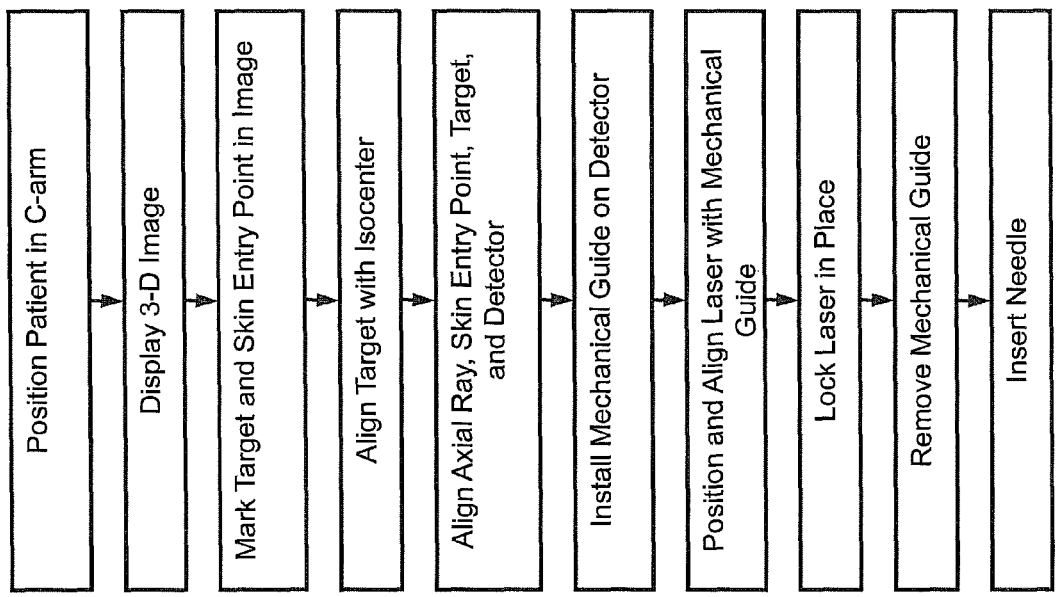
FIG. 4 shows a flowchart of a second prior-art "bulls-eye view" procedure.

FIG. 4 shows a flowchart of a second embodiment of a prior-art "bulls-eye view" method. This method is simpler because a needle is not used for initial positioning and alignment of the laser beam. Steps 402-410 are similar to steps 302-310. First, in step 402, the patient 110 is positioned in the C-arm 102. In step 404, a 3-D image of the patient is rendered from a previously acquired 3-D volume dataset and displayed on a monitor. In step 406, the positions of the target and skin entry point are marked on the display with graphical markers. In step 408, the target is aligned with the isocenter 116. In step 410, the axial ray 112, skin entry point, target, and center pixel of the detector 106 are aligned.

In step 412, a mechanical guide is installed over the center pixel of the detector 106. In step 414, a single-headed laser, which may be mounted on a mechanical arm, is positioned in the mechanical guide. The mechanical guide centers the axis of the laser beam over the center pixel of the detector and aligns the axis of the laser beam orthogonal to the plane of the detector. The axis of the laser beam is therefore collinear with the planned needle trajectory. In step 416, the laser is locked in place. In step 418, the mechanical guide is removed. Finally, in step 420, the needle is inserted while maintaining the axis of the needle collinear with the axis of the laser beam.

The second prior-art method does not require alignment of a needle under real-time fluoroscopy to align the laser. However, it still requires aligning the target with the isocenter. Furthermore, installing, aligning, and removing the mechanical guide on the detector is also difficult and time consuming.

In the prior-art procedures described above, some of the complications arise because the laser beam impinges on a single reference point, such as a pre-aligned needle or mechanical guide. Alignment of the axis of the laser beam with the pre-aligned needle is performed while sighting along the laser beam. This step is difficult and time consuming. Installation and removal of a mechanical guide are both cumbersome and time consuming. The inventors have recognized that alignment procedures may be greatly simplified by defining two reference points, and using a laser assembly emitting two laser beams.

FIG. 5A and FIG. 5B illustrate embodiments of the invention. In FIG. 5A and FIG. 5B, curve 502 represents the skin surface of the patient 110; point 506 represents the skin entry point at which a needle is inserted; point 504 represents the target; and dashed line 508 represents the desired needle trajectory. In FIG. 5A, dual-headed optical source 510 emits two independent collimated beams. In one embodiment, dual-headed optical source 510 may comprise a single lamp and two collimator lens assemblies. In another embodiment, shown in FIG. 5A, dual-headed optical source 510 comprises single-headed optical source 510A and single-headed optical source 510B. Each single-headed optical source comprises a lamp and a collimator lens assembly. In an advantageous embodiment, dual-headed optical source 510 is a laser source, which, for example, may comprise a single laser transmitter emitting two laser beams, or two laser transmitters, each of which emits a single laser beam. In general, the axis of the collimated beam 512 emitted from optical source 510A and the axis of the collimated beam 514 emitted from optical source 510B are not necessarily collinear. In some embodiments, the spacing and angle between the two axes may be restricted to values within a user-defined maximum range.

Dual-headed optical source 510 is positioned between skin entry point 506 and an external reference surface 516, on which external reference point 518 is located. In an embodiment described below, external reference surface 516 is cover 204 of X-Ray detector 106. The position and orientation of external reference surface 516 is adjustable. A visual index mark is physically marked on external reference surface 516. The visual index mark, for example, may be an indent, scribe mark, or ink mark on cover 204. Herein, the position of the visual index mark is fixed relative to the external reference surface 516. Herein, "external reference point", such as external reference point 518, refers to a point in space, not to the visual index mark itself. The position of the external reference point, for example, is relative to the positions of target 504 and skin entry point 506. In embodiments below, the external reference surface 516 may be positioned and oriented such that the visual index mark is coincident with an external reference point. Herein, the position of the external reference point is "calculated" by an instrument system. Depending on the procedure, the position may be calculated from the previously acquired 3-D volume dataset, the geometry of the instrument system, and other parameters. The instrument system may also move external reference surface 516 such that the visual index mark is coincident with the calculated external reference point. In an advantageous embodiment described below, the instrument system is a C-arm X-Ray system.

Adjustment mechanisms permit collimated beam 512 to be aimed at skin entry point 506 and collimated beam 514 to be simultaneously aimed at reference point 518. For example, the entire dual-headed optical source 510 may be held by a mounting assembly comprising base 530, mechanical arm 532, and bracket 534. Base 530 may be bolted onto a suitable rigid surface such as a C-arm or table frame. Mechanical arm 532 may be loosened to allow free positioning and alignment of dual-headed optical source 510. Mechanical arm 532 may then be tightened to lock the position and alignment of dual-headed optical source 510. Collimated beam 512, collimated beam 514, and external reference point 518 may be configured such that, if collimated beam 512 impinges on skin entry point 506, and if collimated beam 514 simultaneously impinges on external reference point 518, then the axis of collimated beam 512 is collinear with needle trajectory 508. Needle guidance is performed by inserting the needle such that the axis of the needle is maintained to be collinear with the axis of collimated beam 512 during insertion.

FIG. 5B shows an advantageous embodiment. Dual-headed optical source 520 is a fixed assembly which emits laser beam 522 and laser beam 524. The two beams point in opposite directions, and the axes of the two beams are collinear. External reference surface 526 is positioned and oriented such that it is orthogonal to needle trajectory 508, the needle trajectory 508 intersects the external reference surface 526 at external reference point 528, and the visual index marker on external reference surface 526 is coincident with external reference point 528. The position of external reference point 528 has been calculated such that, when laser beam 522 is aimed at skin entry point 506, and laser beam 524 is simultaneously aimed at reference point 528, the axis of laser beam 522 is collinear with the needle trajectory 508. Needle guidance is performed by inserting the needle such that the axis of the needle is maintained to be collinear with the axis of collimated beam 522 during insertion.

The adjustment mechanism for aiming the beams comprises mechanical arm 532 described above. In one embodiment, mechanical arm 532 is adjusted manually. In another embodiment, the mechanical arm 532 is mounted on a stage which may be adjusted mechanically or electromechanically. In a third embodiment, the mechanical arm 532 may be a computer-controlled robotic arm.

In practice, axes which are desired to be ideally collinear may not be truly collinear. Deviations from true collinearity, for example, may arise from manufacturing tolerances which may affect the collinearity of collimated beam 522 and collimated beam 524. Deviations from true collinearity, for example, may also arise from the precision in which mechanical arm 532 may be adjusted. The precision may affect the collinearity of collimated beam 522 and needle trajectory 508. Herein, "collinear" axes refer to "substantially collinear" axes. Two axes are "substantially collinear" if the deviation from true collinearity is such that the actual trajectory along which the needle is guided is within an acceptable tolerance of the ideal needle trajectory 508 defined by the line running between skin entry point 506 and target 504. The acceptable tolerance is a function of the IR procedure and is set by the appropriate medical staff responsible for the IR procedure.

Figure 6A:
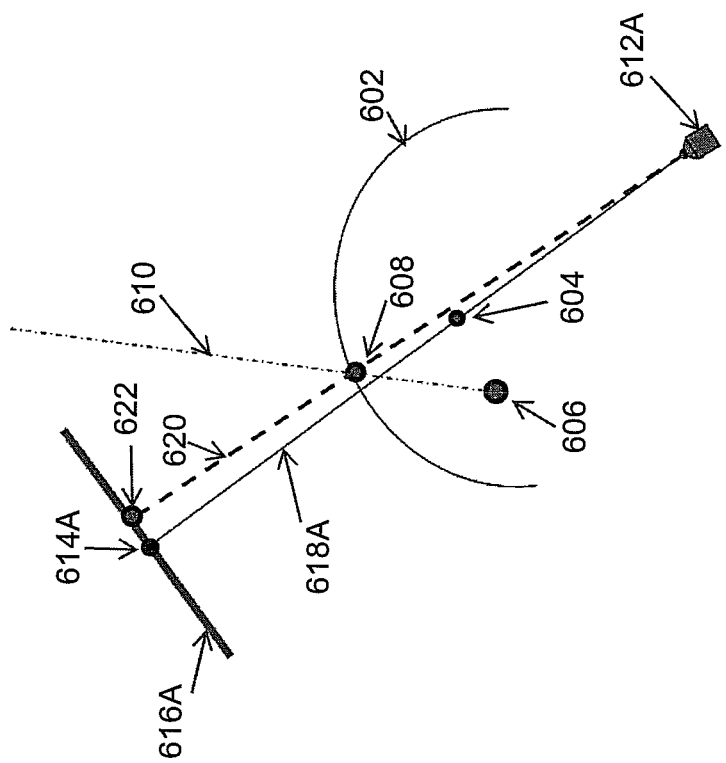
FIG. 6A shows a schematic of an initial C-arm geometry.
Figure 6B:
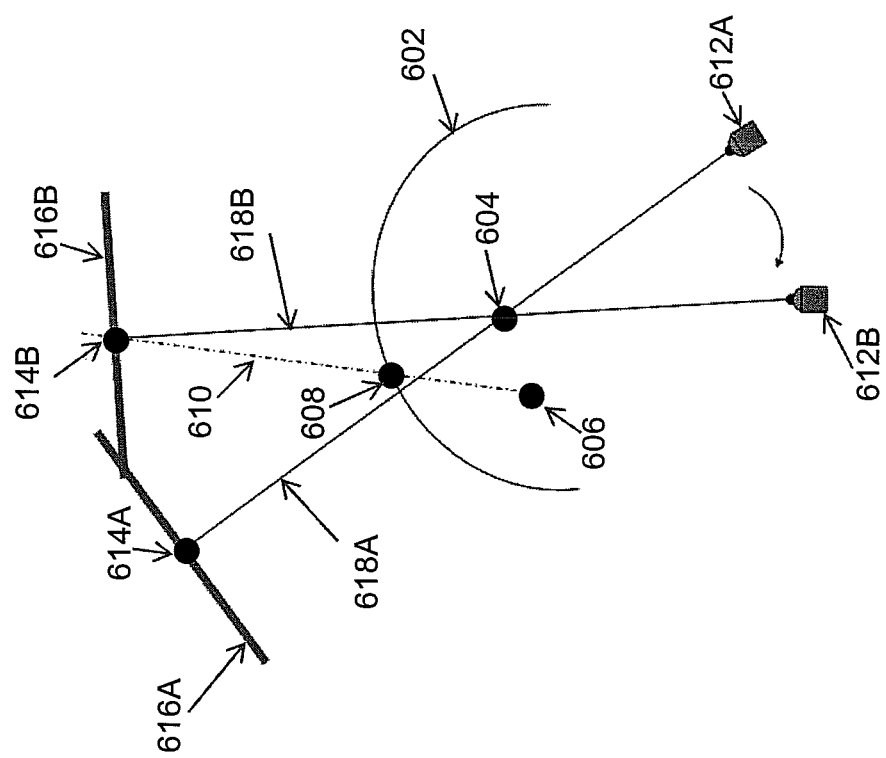
FIG. 6B shows a schematic of a rotated C-arm geometry.
Figure 6C:
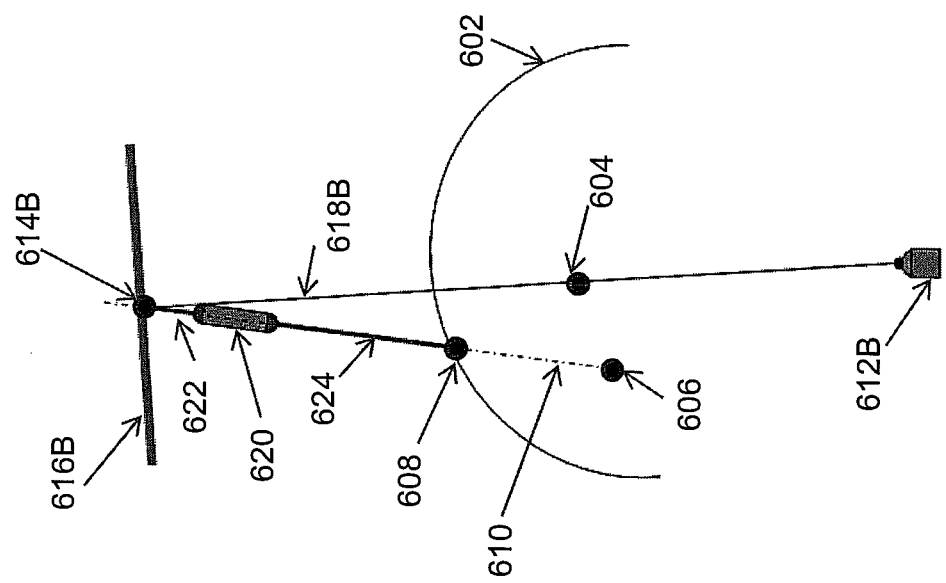
FIG. 6C shows a schematic of a geometry for needle guidance with a dual-headed laser and a C-arm X-Ray system; and,
FIG. 7 shows a flowchart for a needle guidance procedure using a dual-headed laser and a C-arm X-Ray system.
Figure 7:
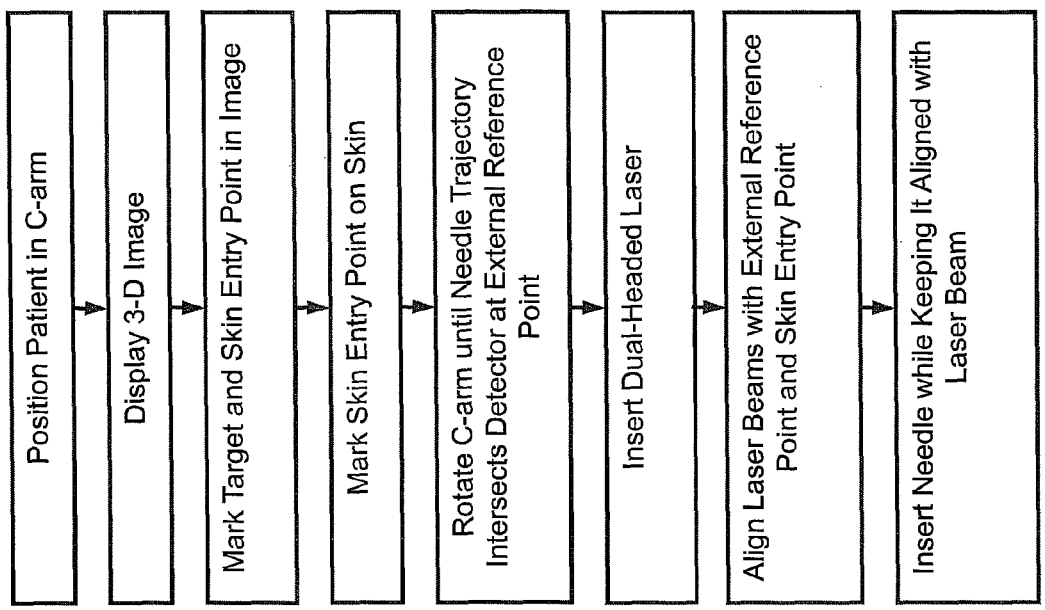

An embodiment of the invention is further illustrated in FIGS. 6A-6C, and described in the corresponding flowchart shown in FIG. 7. FIG. 6A is a graphical representation of the initial C-arm system geometry during an interventional procedure. Curve 602 represents the skin surface of the patient 110; point 608 represents the skin entry point at which a needle is inserted; point 604 represents the isocenter 116 of the C-arm system; point 606 represents the target; and dashed line 610 represents the desired needle trajectory.

An embodiment of the invention follows the sequence of steps in the flowchart in FIG. 7. First, in step 702, the patient 110 is placed on table 108 and positioned in C-arm 102. In step 704, a 3-D image of the region of interest is rendered from a previously acquired 3-D volume dataset and displayed on a monitor. In step 706, the positions of the target and skin entry point, as determined from previous diagnostics, are marked on the display with graphical markers. In step 708, the skin entry point on the actual patient's skin is physically marked with, for example, a pen.

In step 708, various techniques may be used to physically locate and mark the skin entry point on the actual patient's skin, which corresponds to the skin entry point shown in a graphical marker in the display. Details of one embodiment are illustrated in FIG. 6A. X-Ray source 612A transmits the axial ray 618A through the patient 110 to X-Ray detector 616A. The axial ray 618A passes through isocenter 604 and impinges orthogonally on detector 616A at its center pixel 614A, which is marked with a visual index mark. In other embodiments, a location other than the center pixel may be used, and the visual index mark may be positioned at another location on detector 616A. In this procedure, it is not necessary to align isocenter 604 with target 606. In this example, the axial ray 618A does not necessarily pass through the skin entry point 608. The dashed line 620 represents a group of oblique rays which pass through skin entry point 608 and impinge obliquely on detector 616A in an approximately circular region 622. The patient 110 is viewed under live fluoroscopy, and the live fluoroscopic image is superimposed onto the 3-D image and displayed on the monitor. Within the 3-D image is the graphical marker indicating the position of the desired skin entry point. A radiopaque (high X-Ray absorption) pointer such as the tip of a scissors is then used to probe the skin. The tip of the pointer, as viewed in the live fluoroscopic image, is moved on the actual patient's skin until the fluoroscopic image of the tip is aligned with the graphical marker in the superimposed 3-D image. The skin entry point is then marked on the actual patient's skin with a physical marker, such as a pen.

In the example described above, the physical skin entry point was marked using X-Ray fluoroscopy. One skilled in the art may develop other methods for locating and physically marking the skin entry point. For example, a point in the 3-D image may be geometrically correlated with a physical point on the patient. A laser system may be configured such that the physical skin entry point corresponding to the skin entry point in the 3-D image is illuminated with a laser beam. The illuminated spot is then marked with a pen.

In step 710, the C-arm is rotated such that the needle trajectory intersects the detector at the center pixel. This alignment procedure is illustrated in FIG. 6B. The initial positions of the X-Ray source 612A, detector 616A, center pixel 614A, and axial ray 618A are the same as those shown in FIG. 6A. The C-arm is then rotated until the needle trajectory 610, defined by the straight line between skin entry point 608 and target 606, intersects the detector 616B at its center pixel 614B. In the new (rotated) positions, 612B is the X-Ray source, 616B is the detector, 614B is the center pixel, and 618B is the axial ray. The C-arm X-Ray system calculates the correct position of the external reference point required for the laser alignment procedure described below. The C-arm X-ray system then rotates the C-arm until center pixel 614B (marked with a visual index mark) is coincident with the calculated external reference point.

Referring to FIG. 6C, in step 712, a dual-headed laser body 620 is inserted between the patient 110 and the detector 616B. In one embodiment of the invention, the laser body 620 is clamped onto a mechanical arm, such as a gooseneck. The base of the gooseneck may be mounted in various places, such as the C-arm 102 or an equipment frame. The mechanical arm may be loosened to allow free movement of the laser body 620, and then tightened to lock the laser body 620 in place. In step 714, laser beam 622 and laser beam 624 are both turned on. The mechanical arm is loosened, and laser body 620 is aligned such that laser beam 622 impinges on center pixel 614B, and laser beam 624 impinges on skin entry point 608. As discussed above, both center pixel 614B and skin entry point 608 were previously physically marked. In one embodiment of the invention, the laser is manually aligned. In a second embodiment, the mechanical arm is mounted on a stage which may be adjusted mechanically or electromechanically. In a third embodiment, the mechanical arm may be a computer-controlled robotic arm.

After alignment, the laser body 620 is locked into place. The axis of laser beam 624 is now collinear with needle trajectory 610. Finally, in step 716, the needle is inserted while maintaining the axis of the needle collinear with the axis of laser beam 624. In one embodiment of the invention, laser beam 624 impinges directly on the hollow needle. In another embodiment, a temporary cap with a reference mark is placed over the upper end of the needle. The axis of laser beam 624 is aimed at the reference mark. After the needle has been inserted, the cap is removed.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for guiding a needle having a tip, an upper end, and an axis, during insertion of said needle along a needle trajectory defined by a skin entry point at a first location and a target at a second location, comprising the steps of:
   positioning, between said skin entry point and an external reference point, a dual-headed optical source to emit a first collimated beam in a first direction and a second collimated beam in a second direction; and
   aligning said dual-headed optical source such that the first collimated beam impinges on said skin entry point and the second collimated beam impinges on said external reference point, and such that the axis of the first collimated beam is substantially collinear with the needle trajectory; and
   positioning the tip of said needle on said skin entry point such that the axis of said needle is substantially collinear with the needle trajectory.

2. The method of claim 1 wherein said first collimated beam and said second collimated beam are laser beams.

3. The method of claim 1 wherein
said first direction is substantially opposite to said second direction and wherein the axis of the first collimated beam is substantially collinear with the axis of the second collimated beam.

4. The method of claim 1 wherein said external reference point is calculated by a processor in a C-arm X-Ray system.

5. The method of claim 4 wherein said C-arm X-Ray system positions an X-Ray detector such that a visual index mark on said X-Ray detector is positioned at said external reference point.

6. The method of claim 1 wherein said dual-headed optical source is mounted on a mechanical arm and wherein said steps of positioning said dual-headed optical source and aligning said dual-headed optical source further comprise the steps of:
   positioning said mechanical arm; and,
   aligning said mechanical aim.

7. The method of claim 1 wherein said step of positioning said needle such that the axis of said needle is substantially collinear with the needle trajectory further comprises the steps of:
   placing a removable cap with a reference mark on the upper end of said needle; and,
   impinging the first collimated beam on said removable cap such that the axis of the first collimated beam impinges on said reference mark as said needle is positioned.

8. A method for guiding a needle having a tip, an upper end, and an axis, during insertion of said needle along a needle trajectory defined by a skin entry point at a first location and a target at a second location, comprising the steps of:
   positioning, between said skin entry point and an external reference point, a dual-headed laser source emitting a first laser beam in a first direction and a second laser beam in a second direction wherein said first direction and said second direction are substantially opposite and wherein the axis of the first laser beam and the axis of the second laser beam are substantially collinear;
   aligning said dual-headed laser source such that the first laser beam impinges on said skin entry point and the second laser beam impinges on said external reference point, and such that the axis of the first laser beam is substantially collinear with the needle trajectory;
   positioning the tip of said needle substantially on said skin entry point; and
   inserting the needle through said skin entry point along said trajectory such that the axis of said needle remains collinear with the axis of the first laser beam.

9. The method of claim 8 wherein said external reference point is calculated by a processor in a C-arm X-Ray system.

10. The method of claim 9 wherein said C-arm X-Ray system positions an X-Ray detector such that a visual index mark on said X-Ray detector is positioned at said external reference point.

11. The method of claim 8 wherein said dual-headed laser source is mounted on a mechanical arm and said steps of positioning said dual-headed laser source and aligning said dual-headed laser source further comprise the steps of:
   positioning said mechanical arm; and,
   aligning said mechanical aim.

12. The method of claim 8 wherein said step of inserting said needle comprises the steps of:
   placing a removable cap with a reference mark on the upper end of said needle; and,
   impinging the first laser beam on said removable cap such that the axis of the first laser beam impinges on said reference mark as said needle is inserted.

13. An apparatus for guiding insertion of a needle along a needle trajectory from a skin entry point to a target, said apparatus comprising:
   a dual-headed optical source for emitting a first collimated beam in a first direction and a second collimated beam in a second direction, said dual-headed optical source being movable to one or more positions between said skin entry point and an external reference point on an external surface separate from said dual-headed optical source;
   an instrument system for calculating a location of said external reference point; and,
   an adjustment mechanism for aiming said first collimated beam in the first direction at said skin entry point and aiming said second collimated beam in the second direction at said external reference point such that the first collimated beam impinges on said skin entry point and the second collimated beam impinges on said external reference point.

14. The apparatus of claim 13 wherein said dual-headed optical source comprises at least one laser transmitter.

15. The apparatus of claim 13 wherein said instrument system comprises a C-arm X-Ray system.

16. The apparatus of claim 15 wherein said C-arm X-ray system positions an X-Ray detector such that a visual index mark on said X-Ray detector is positioned at said external reference point and
said external reference point is calculated by a processor in said C-arm X-Ray system using system geometry so that an axis of the first collimated beam aimed at the skin entry point is substantially collinear with said needle trajectory.

17. The apparatus of claim 13 wherein said adjustment mechanism is an adjustable mechanical arm.

18. An apparatus for guiding insertion of a needle along a needle trajectory from a skin entry point to a target, said apparatus comprising:
   a dual-headed laser source for emitting a first laser beam in a first direction and a second laser beam in a second direction, wherein said first direction and said second direction are substantially opposite and wherein an axis of the first laser beam and an axis of the second laser beam are substantially collinear;
   an instrument system for calculating a location of said external reference point on an external surface; and,
   an adjustment mechanism for aiming said first laser beam in the first direction at said skin entry point and aiming said second laser beam in the second direction at said external reference point.

19. The apparatus of claim 18 wherein said instrument system is a C-arm X-Ray system.

20. The apparatus of claim 19 wherein said C-arm X-ray system positions an X-Ray detector such that a visual index mark on said X-Ray detector is positioned at said external reference point.

21. The apparatus of claim 18 wherein said adjustment mechanism is an adjustable mechanical arm.

\* \* \* \* \*